US012584094B2

(12) United States Patent
Basu et al.

(10) Patent No.: US 12,584,094 B2
(45) Date of Patent: Mar. 24, 2026

(54) MICROFLUIDIC AND MEMS CELL LYSIS SYSTEM AND METHOD

(71) Applicants: The University of Chicago, Chicago, IL (US); UChicago Argonne, LLC, Chicago, IL (US)

(72) Inventors: Anindita Basu, Chicago, IL (US); Abhiteja Konda, San Jose, CA (US); Pavani Vamsi Krishna Nittala, Westmont, IL (US); Supratik Guha, Chicago, IL (US)

(73) Assignees: The University of Chicago, Chicago, IL (US); UChicago Argonne, LLC, Chicago, IL (US)

( * ) Notice: Subject to any disclaimer, the term of this patent is extended or adjusted under 35 U.S.C. 154(b) by 525 days.

(21) Appl. No.: 18/252,529

(22) PCT Filed: Nov. 9, 2021

(86) PCT No.: PCT/US2021/058570
§ 371 (c)(1),
(2) Date: May 10, 2023

(87) PCT Pub. No.: WO2022/103728
PCT Pub. Date: May 19, 2022

(65) Prior Publication Data
US 2023/0407235 A1      Dec. 21, 2023

Related U.S. Application Data

(60) Provisional application No. 63/112,984, filed on Nov. 12, 2020.

(51) Int. Cl.
C12N 1/06        (2006.01)
B01L 3/00        (2006.01)
C12N 1/066       (2026.01)

(52) U.S. Cl.
CPC ........ *C12N 1/066* (2013.01); *B01L 3/502715* (2013.01); *B01L 2200/025* (2013.01); *B01L 2300/123* (2013.01); *B01L 2400/0487* (2013.01)

(58) Field of Classification Search
CPC ....... C12N 1/066; C12M 23/16; C12M 47/06; B01L 3/502715; B01L 3/502761;
(Continued)

(56) References Cited

U.S. PATENT DOCUMENTS 6,358,474 B1 * 3/2002 Dobler ..................... G01N 1/34
435/270
6,695,236 B2    2/2004 Gazeau
(Continued)

OTHER PUBLICATIONS

Brown et al., "Current techniques for single-cell lysis," J. R. Soc., Interface, (Apr. 2008), S131-S138, 5(Suppl 2), published online Apr. 15, 2008.
(Continued)

*Primary Examiner* — Michael L Hobbs
(74) *Attorney, Agent, or Firm* — Leydig, Voit & Mayer, Ltd.

(57)        ABSTRACT

A system and method for mechanical processing of cells includes using a frame (102) forming an inlet channel (104), an outlet channel (106), and a processing chamber (108) fluidly connected between the inlet and outlet channels, wherein the processing chamber includes an anvil surface (112) formed on the frame. A hammer (110) mounted on the frame has a processing surface disposed in opposed relation to the anvil surface. The hammer is configured to move relative to the anvil surface. An actuator connected to the frame and operably associated with the hammer operates to move the hammer relative to the anvil surface and in close proximity to the anvil surface, wherein the hammer operates between a retracted position in which the processing surface
(Continued)

is at a distance from the anvil surface, and an extended position in which the processing surface abuts the anvil surface.

12 Claims, 9 Drawing Sheets

(58) Field of Classification Search
CPC ........... B01L 2200/025; B01L 2200/12; B01L 2300/123; B01L 2400/0487
See application file for complete search history.

(56) References Cited

U.S. PATENT DOCUMENTS

| | | | |
|---|---|---|---|
| 7,960,167 | B2 | 6/2011 | Aizenberg et al. |
| 10,160,947 | B2 * | 12/2018 | Bourdat ................. G01N 1/286 |
| 2017/0280741 | A1 | 10/2017 | Malkin et al. |

OTHER PUBLICATIONS

Carlo et al., "Reagentless mechanical cell lysis by nanoscale barbs in microchannels for sample preparation," Lab Chip, (2003), 287-291, 3(4).

Choi et al., "On-chip Extraction of Intracellular Molecules in White Blood Cells from Whole Blood," Sci. Rep., 15167, 12 pp., 5(1), (Oct. 2015), published online Oct. 14, 2015.

Grigorov et al. "Review of Microfluidic Methods for Cellular Lysis," Micromachines, (Apr. 2021), 498, 27 pp. 12(5).

Huang et al., "MEMS-based sample preparation for molecular diagnostics," Anal. Bioanal.Chem., (2002), 49-65, 372(1).

Huh et al., "Microfluidic cell disruption system employing a magnetically actuated diaphragm," Electrophoresis, (2007), 4748-4757, 28(24).

Kido et al., "A novel, compact disk-like centrifugal microfluidics system for cell lysis and sample homogenization," ColloidsSurf., B, (2007), 44-51, 58(1).

Kim et al., "Cell lysis on a microfluidic CD (compact disc)," Lab Chip, (2004), 516-522, 4(5).

Nittala et al., "Integration of silicon chip microstructures for inline microbial cell lysis in soft microfluidics," Lab Chip, (Apr. 2023), 2327-2340, 23.

Thompson et al., "Microfluidics for single-cell genetic analysis," Lab Chip, (2014), 3135-3142, 14.

U.S. Patent and Trademark Office, International Search Report, dated Feb. 7, 2022, corresponding to International Application No. PCT/US2021/058570, (from which the present application claims priority), 3 pp.

U.S. Patent and Trademark Office, Written Opinion dated Feb. 7, 2022, corresponding to International Application No. PCT/US2021/058570, (from which the present application claims priority), 8 pp.

Whitesides, "The origins and the future of microfluidics," Nature, (2006), 368-373, 442.

* cited by examiner 302
i
Silicon
Si wafer 303
ii
Silicon
Black silicon in Deep etcher

300

304

306 iii 30.76nm

Device 1

Device 2

Layer 2

Terminal to test
electrical contact

Layer 1

500

| tilt | HV | WD | mag ■ | det | mode | HFW | |
|------|------|--------|---------|-----|------|---------|---------|
| 45 ° | 5.00 kV | 4.1 mm | 8 000 x | ETD | SE | 16.0 µm | 5 µm |

504

502

506

MICROFLUIDIC AND MEMS CELL LYSIS SYSTEM AND METHOD

CROSS-REFERENCE TO RELATED APPLICATIONS

This application is a U.S. National Phase of International Patent Application No. PCT/US2021/058570, filed Nov. 9, 2021, which claims priority to U.S. Provisional Patent Application Ser. No. 63/112,984, which was filed on Nov. 12, 2020, each of which is incorporated herein in its entirety by this reference for all purposes.

STATEMENT REGARDING FEDERALLY SPONSORED RESEARCH OR DEVELOPMENT

This invention was made with government support under AI158157 awarded by the National Institutes of Health, and N00014-18-1-2869 awarded by the Office of Naval Research. The government has certain rights in the invention.

BACKGROUND OF THE INVENTION

Single cell genomics is an emerging field of research that has found rapid and wide use in research, industry and medicine. Single cell techniques can characterize a population of cells at the epigenomic, transcriptomic or proteomic level at single cell resolution. These techniques are crucial in characterizing genomic heterogeneity between individual cells comprising a cell population, including clonal population. This heterogeneity is expressed in differential gene expression, protein production, or cell fitness. Intra-cellular heterogeneity exists in any microbial cell population in response to the ever-changing, complex environment. To quantify this variation, one needs to be able to transcriptionally profile each microbial species at single cell resolution and high throughput. Currently, no such technology exists.

BRIEF SUMMARY OF THE INVENTION

The present disclosure is generally directed to a system and method that integrates semiconductor-based components and functionality into soft microfluidics for cell lysis and other biological applications. In one embodiment, a micro-fabricated silicon chip is integrated into soft microfluidics either for passive or active applications. In an embodiment, a piezoelectric-drive driven micro-fabricated silicon chip with sharp tip arrays is used to physically break cells (lysis) in a microfluidic device to extract contents of the cell. These cells, for instance, could be microbes.

In general, lysis is an important process step in many cellular processing applications. This invention provides a scalable, controllable, in-line lysis tool for integration with microfluidic devices.

Additional aspects of the invention are as described herein.

BRIEF DESCRIPTION OF THE SEVERAL VIEWS OF THE DRAWING(S)

FIG. 1A is a cross-sectional view of a device before piezo actuation, and FIG. 1B is a cross sectional view of a device during piezo actuation.

DETAILED DESCRIPTION OF THE INVENTION

While success has been achieved in profiling multicellular eukaryotes, there are challenges to overcome for profiling microbial species—the small cell size (~1 μm) with concomitantly small RNA quantity, and the difficulty in lysis of the strong and adaptive cell wall that allows for unicellular life under harsh environmental conditions (pH, anti-microbial, etc.). The problem of cell lysis is common to all single cell genomic techniques.

In the past, partial success in single cell lysis had been achieved by the targeting microbial species with weaker cell walls, or by targeting specific components of the cell walls using enzymatic lysis. The present disclosure is directed to a system and method in which a hybrid microfluidic+MEMS (micro-electromechanical system) device is used to perform lysis of single microbial cells in an unbiased fashion for downstream genomic analyses. Single cell lysates, which are useful for proteomic and metabolic profiling, PCR based assays, genome sequencing, etc., were used in one embodiment as input for high-throughput single cell RNA-seq.

Disclosed herein are embodiments for devices and processes for incorporation of semiconductor components and functionality into soft microfluidic devices used for a variety of applications. It is noted that these elements can be used for a variety of purposes, such as for measuring parameters, for altering the nature of the microfluidic contents, and for manipulation of the microfluidic contents. These elements can be used for both passive applications, as well as active applications with embedded electronic circuitry in semiconductor devices.

Figures 1A, 1B:
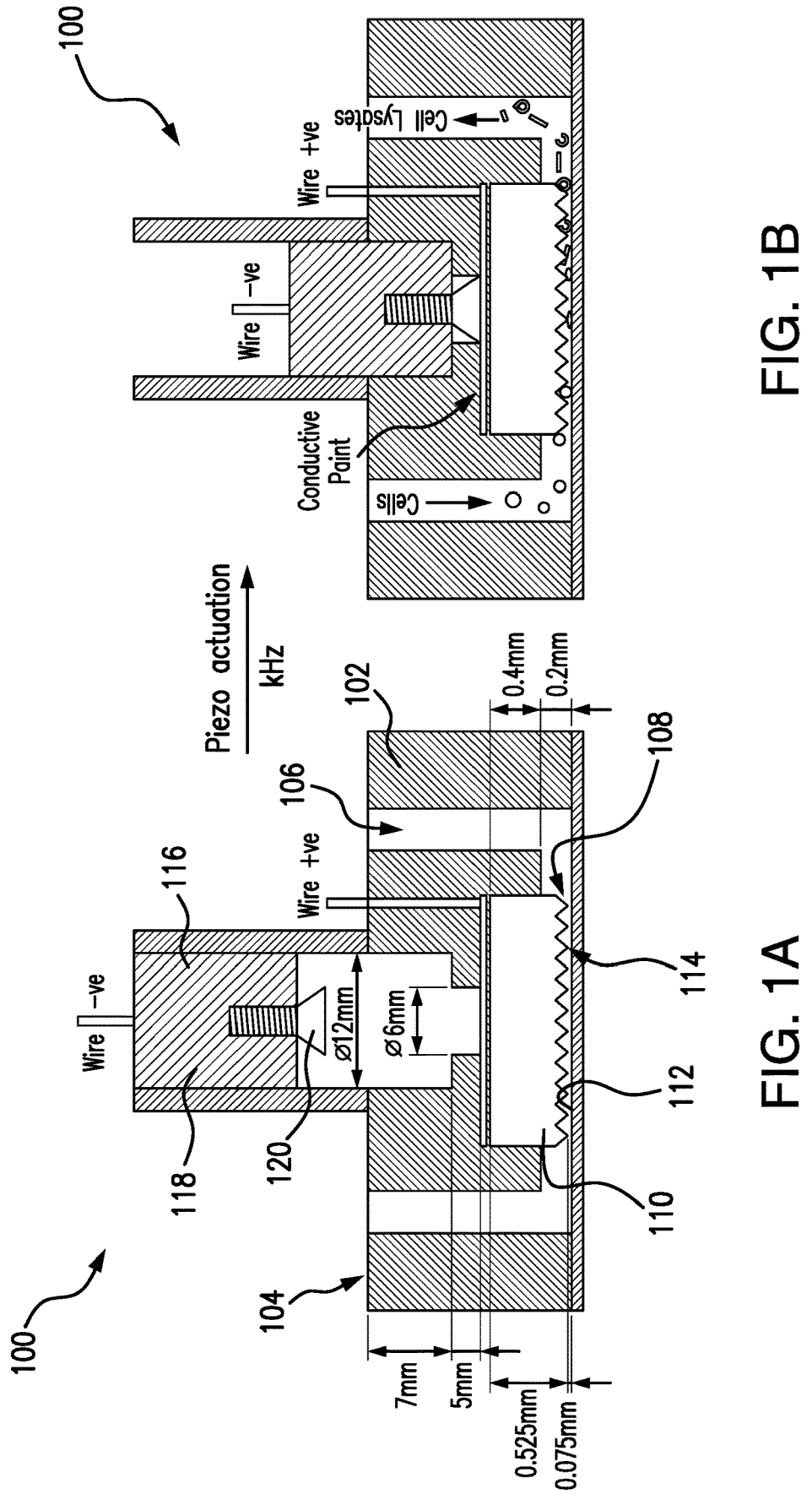
FIGS. 1A and 1B are schematics showing different components of a device in accordance with the disclosure in two operating positions. More specifically.

One example of this approach is the use of the apparatus 100, shown in two operating positions in FIGS. 1A and 1B. In the illustrated exemplary embodiment, the apparatus 100 is embodied as a patterned semiconductor structure with pointed pyramidal structures having piezo electric activation, but other structures can also be used. For example, the pointed pyramidal structures can be omitted such that two opposed flat surfaces are presented, or the pointed pyramidal structures can be replaced with other shapes such as cylindrical structures, frustoconical structures, or ridges extending parallel or at different angles relative to one another carved onto a flat surface, and other shapes. Gaps or features performing the fracturing can be dimensioned anywhere between 0.01 μm and 100 μm, and be spaced apart by gaps having a depth between 0.01 μm and 1000 μm (1 mm). Moreover, while a piezo electric activation arrangement is shown here, other activation arrangements can be used, including but not limited to pneumatic, hydraulic, electro-mechanical, and/or mechanical drive arrangements can be used.

In the embodiment shown here, which is non-limiting, the plurality of pointed structures (PPS) is formed to create an array of sharp protruded tips on a silicon wafer, and the device is embedded in a microfluidic channel. Motion resulting from a piezoelectric actuator then drives the PPS back and forth towards the opposing wall of the microfluidic channel to perforate and lyse the cell walls of microbes that are flowing through the channel. It should be appreciated that the motion that drives the PPS can be carried out in one direction and/or in more than one direction simultaneously. In an illustrative example, the motion of the PPS can be a reciprocal vertical motion to crush the microbes, while in other examples the motion can include in addition to or instead of the vertical motions other types of motions that include relative motion between an anvil and the hammer (e.g., the PPS) having 3 degrees of freedom so that normal motion, shear motion, and/or rotational or grinding interaction between the hammer and anvil surfaces is used to lyse the microbes. The dimensions shown in FIG. 1A are exemplary and representative and should not be construed as limiting or required. The pointed nature of the pyramids enables the loading of high stress concentrations on the cell walls over small areas, thereby leading to perforation or fracture or cracking of the cell walls. Other shapes can also have a desired cracking performance, for example, blunted cylindrical features (frustoconical), pillars, ridges, or randomly spiked surfaces, as will be described hereinafter.

It is contemplated that the PPS structures are exemplary and should not be understood as required or limiting. In general, the systems and methods in accordance with the disclosure can utilize any other type of pointed or blunt structure that will mechanically interact with microbes and operate to crush microbes using a small footprint to increase crushing pressure, for example, a truncated pyramid which can deliver a high crushing force per unit area; a blade-like or knife-edge structure that will operate to impale microbes; or a combination of both blunt and sharp-edged structures that may operate to both crush and impale microbes as the microbes pass through a processing area.

Figure 7:
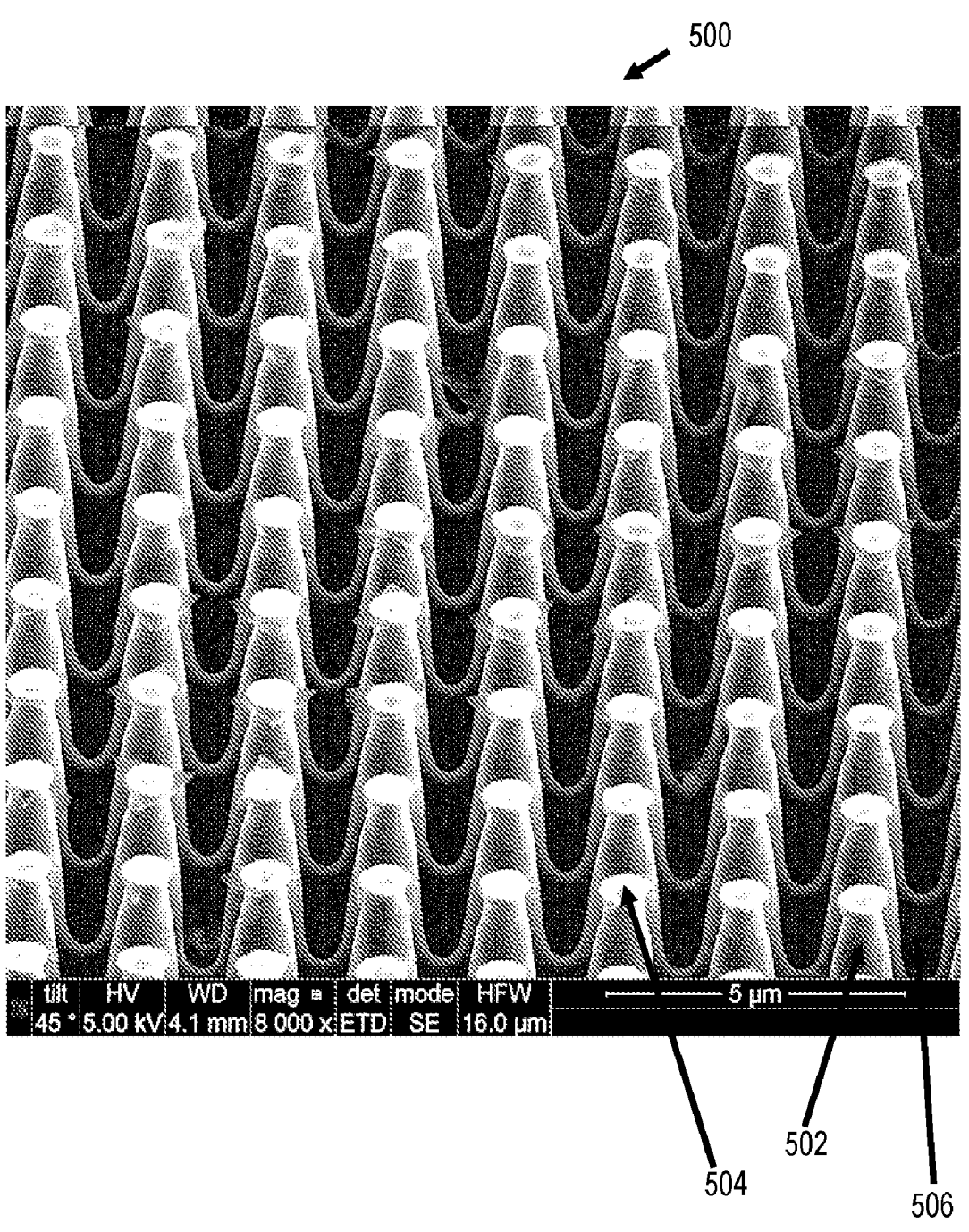
FIG. 7 is an alternative embodiment for a fabricated hammer substrate in accordance with the disclosure.
Figure 8:
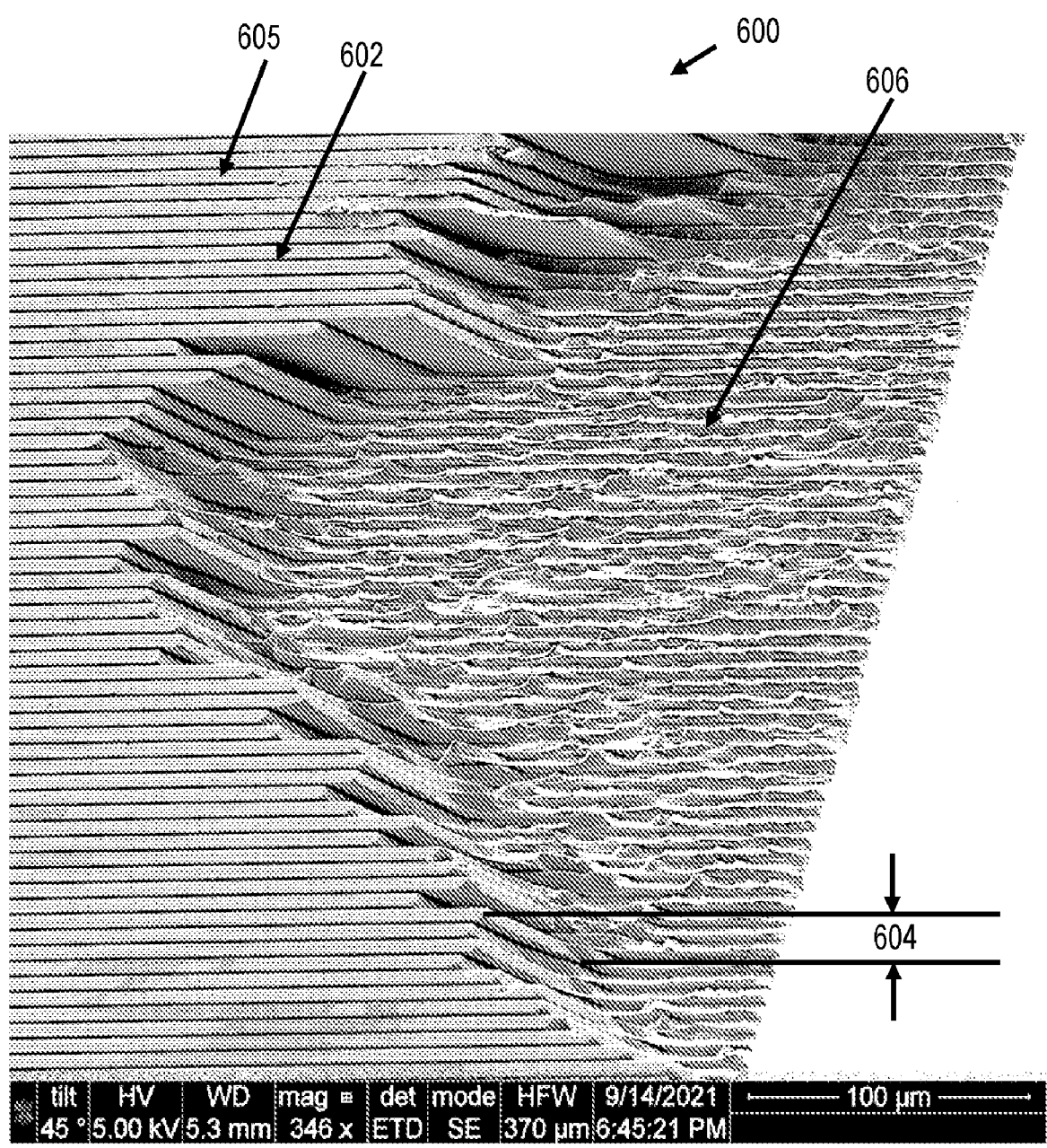
FIG. 8 is another alternative embodiment for a fabricated hammer substrate in accordance with the disclosure.

In general, "pointed structures" as used herein refers to structures formed on the processing surface of the hammer, as described below, which can include (i) truncated structures in ordered arrangement, (ii) arrays of blade-like knife edge structures or (iii) any ordered or disordered array of structures that allow the hammer to deliver concentrated stresses over small areas to the microbial surfaces. An example of a fabricated substrate having repeating truncated structures is shown in FIG. 7, and an example of arrays of blade-like structures is shown in FIG. 8, both described as exemplary embodiments at the end of the present disclosure. Such pointed structures can be made using lithographic patterning, or by chemical or electrochemical treatment of the wafer surface to create surfaces with asperities that can deliver such high stress concentrations. The pointed structures can generally be formed as any type of regular or irregular structure that offers a plurality of high asperity features. It is contemplated that any such pointed structures will have 3 dimensional features with a high aspect ratio (feature height:feature width ratio).

In the illustrated embodiment, the apparatus 100 includes a frame 102 having an inlet channel 104 and outlet channel 106 formed therein. The inlet and outlet channels 104 and 106 communicate through a processing chamber 108 defined between a hammer substrate 110 and an anvil surface 112. The hammer substrate 110 includes a plurality of pounding structures 114 that are oriented towards the anvil surface 112. The hammer substrate 110 and pounding structures 114 formed on a processing surface of the hammer substrate 110 together form a hammer structure that moves relative to an anvil surface. The pounding structures 114 are exemplary and can be entirely or partially replaced by another structures such as a blunt-end structure that crushes microbes, for example, a truncated cone or pyramid structure, or a pointed-end structure having sharp tips to perforate or impale microbes. The hammer substrate 110 is slidably disposed in the frame 102 for reciprocal motion towards and away the anvil surface 112. A piezo-electric actuator 116 includes a piezoelectric element 118 mounted on the frame 102 and a linkage 120 configured to contact the hammer substrate 110. During operation, the piezoelectric element 118 can activate the linkage 120 and impart a reciprocating motion on the hammer substrate 110, which acts as a hammer and moves towards and away the anvil surface 112. Such structures can be fabricated using standard semiconductor processing, as described later. The motion of the embedded semiconductor pyramids can be modulated using the piezoelectric drive to be able to perforate and/or crush microbes via a mechanical process. The Hammer substrate 110 can be made of any rigid material whose surface can be patterned to create the PPS or similar features. Exemplary materials for the substrate include silicon, ceramic oxide substrates, and other semiconductors such as GaAs, or a combination of such materials.

For perforating microbes, the microbes are provided to the apparatus 100 through the inlet opening or inlet channel 104 and pass through the processing chamber 108 and over the anvil surface 112 while the hammer substrate 110 is actively reciprocating to crush and/or impale the microbes against the anvil surface. As previously discussed, the relative motion of the hammer substrate 110 relative to the anvil surface 112 can be along a single direction and also along multiple directions in both a reciprocal fashion and also a rotating fashion. A retracted position of the hammer substrate 110 is shown in FIG. 1A, and an extended or crushing position of the hammer substrate 110 is shown in FIG. 1B. Crushed or perforated microbe material then exits the apparatus (100) through the outlet channel 106.

While a piezo-electric actuator is shown in this embodiment, other activation methods and systems can also be used. For example, other types of embedded hardware could be the application of localized electric fields and microwave or radio-frequency (RF) fields, local optical excitation and detection/spectroscopy via integrated chip scale lasers, LEDs and photodetectors, or localized temperature fields via micro-heaters, and the like can also be used.

Figures 2A, 2B:
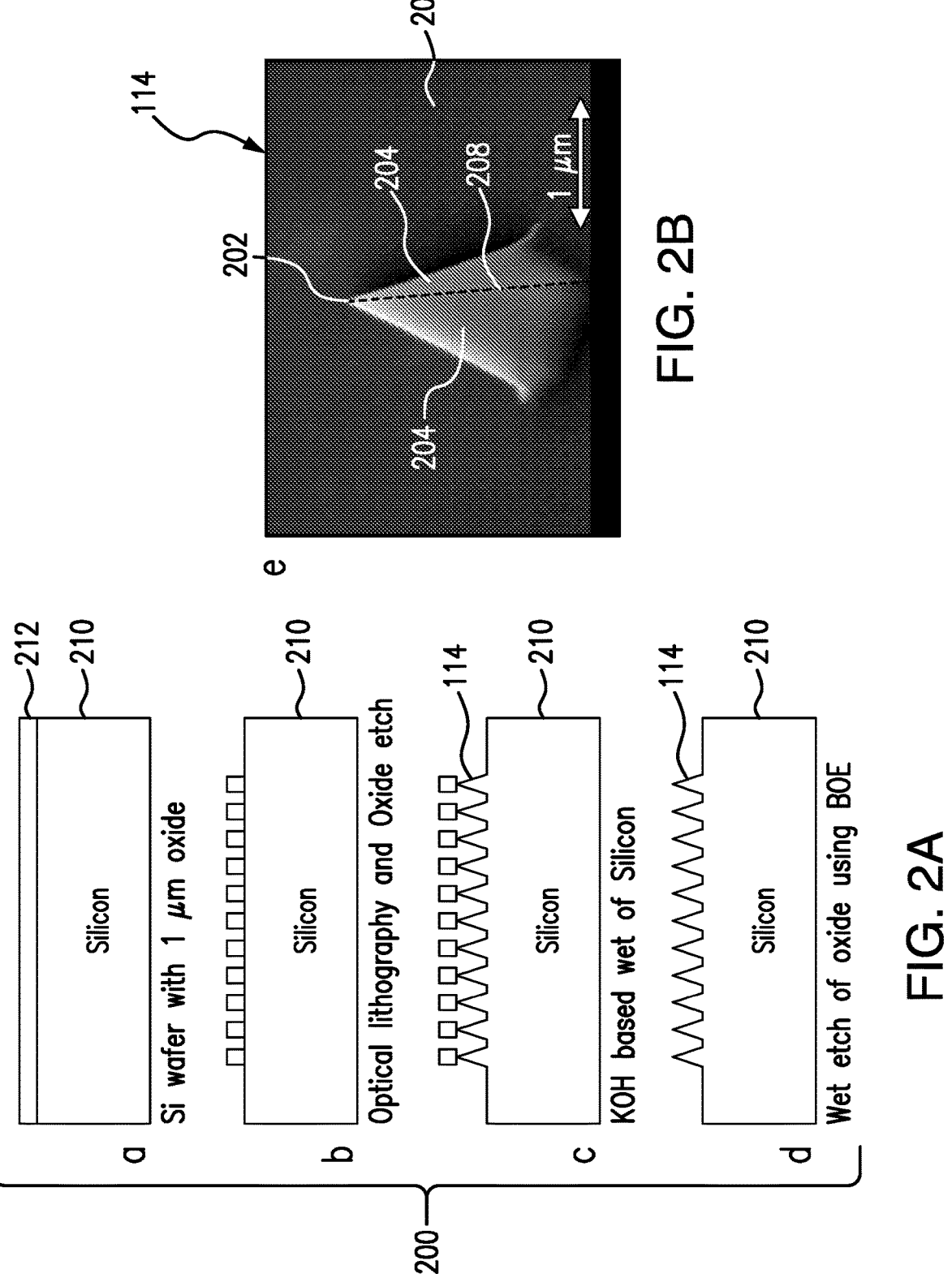
FIG. 2A is a visual illustration of four stages of an exemplary fabrication process for a device in accordance with the disclosure.
FIG. 2B is a view of an exemplary fabricated sharp pyramidal structure in accordance with the disclosure.

FIGS. 2A and 2B illustrate one embodiment for a process flow to manufacture the hammer substrate 110. The process involves patterning Silicon (Si) wafers resulting in the pyramid like structures or "jaws," which are referred to herein relative to FIG. 1 as pounding structures 114. In reference to these figures, one process for fabrication of the features or structures that effect the pounding of microbes between the hammer and anvil, e.g., the pounding structures 114, is shown.

Figure 3A:
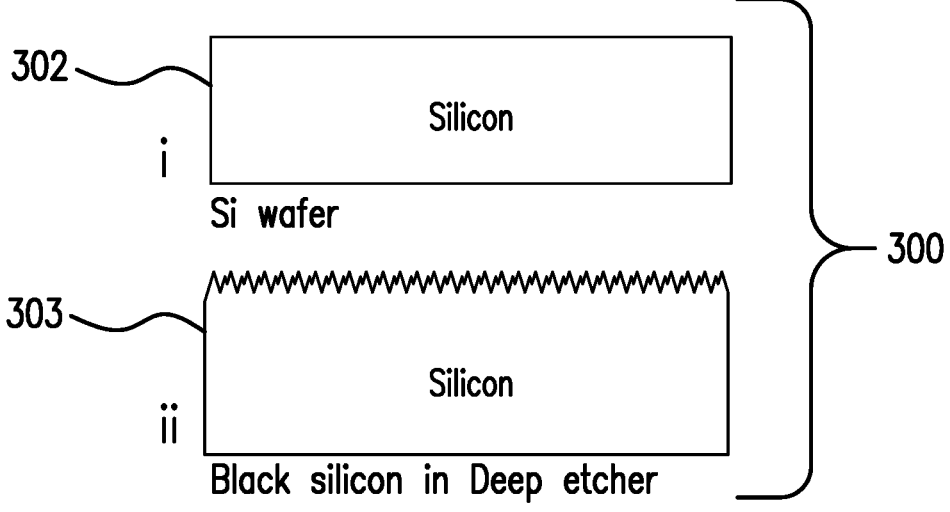
FIG. 3A is a visual illustration of two stages of an alternative fabrication process for a device in accordance with the disclosure.
Figure 3B:
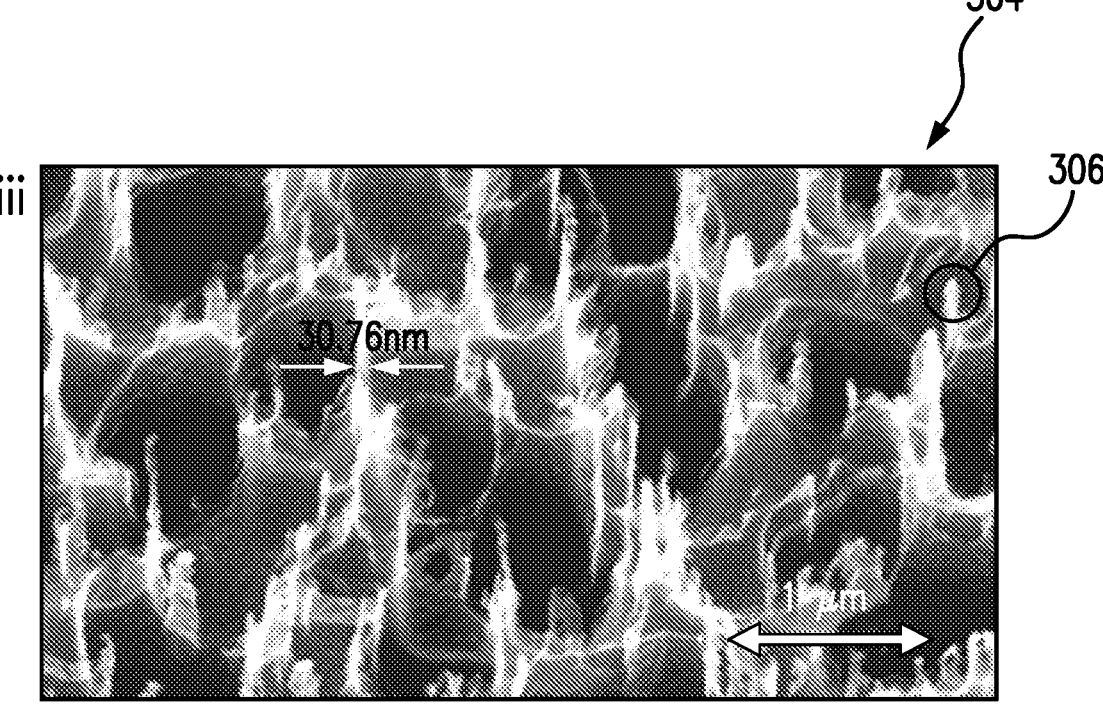
FIG. 3B is a view of an exemplary fabricated sharp pyramidal structure in accordance with the disclosure.

Silicon jaws can be fabricated in various ways. A first approach 200 for fabricating silicon jaws based on systematic silicon pyramidal, cylindrical, conical, frustoconical, or slotted structures is shown in FIGS. 2A and 2B, and a second approach 300, which is based on non-systematic nanometer sharp tips, is shown in FIGS. 3A and 3B. It should be appreciated, however, that the hammer substrate can be made from a different material. For example, metals can also be used and etched as generally described herein to provide suitable features on their surfaces for serving as the hammer substrate 110.

In the first approach shown here, a silicon <100> oriented wafer 210 with 1 μm oxide thickness layer 212 (FIG. 2A(a)) is patterned and the oxide is etched used using inductively coupled plasma reactive ion etching tool (FIG. 2A(b)). Further, after the resist removal and cleaning process, the silicon wafer 210 is etched using KOH etch to form the silicon systematic pyramids or pounding structures 114 (FIG. 2A(c)). Finally, the remaining oxide is etched away using the buffered oxide etchant (FIG. 2A(d)). Scanning electron microscopy image of a KOH etched single silicon tip, which can be considered as one of the pounding structures 114 formed in the hammer substrate 110 (FIG. 1A) can be seen in FIG. 2B(e). In reference to this figure, it can be seen that each of the pounding structures 114 includes a tip 202 with flat, converging faces 204 in a pyramidal arrangement that converge to the tip 202 and raise from a flat substrate surface 206. Shapes other than pyramids can also be used. In this example, edges 208 having a generally straight shape separate adjacent faces 204 but it should be appreciated that, depending on the various etching parameters, the edges 208 may be curved, and can be the faces 204.

In the second approach 300, shown in FIGS. 3A and 3B, a silicon wafer 302 is cleaned using acetone and isopropyl alcohol (IPA) (FIG. 3A(i)). Further, using the modified BOSCH process the wafer 302 is etched using a deep silicon etch tool to form an etched wafer 303, a portion of which is illustrated in FIG. 3B where a black silicon 304 substrate includes raised features 306. As shown in FIG. 3B(iii) using a scanning electron microscope, jagged or sharp non-systematic tips 306 remain on a face of the wafer 303.

Figures 4A, 4B, 4C:
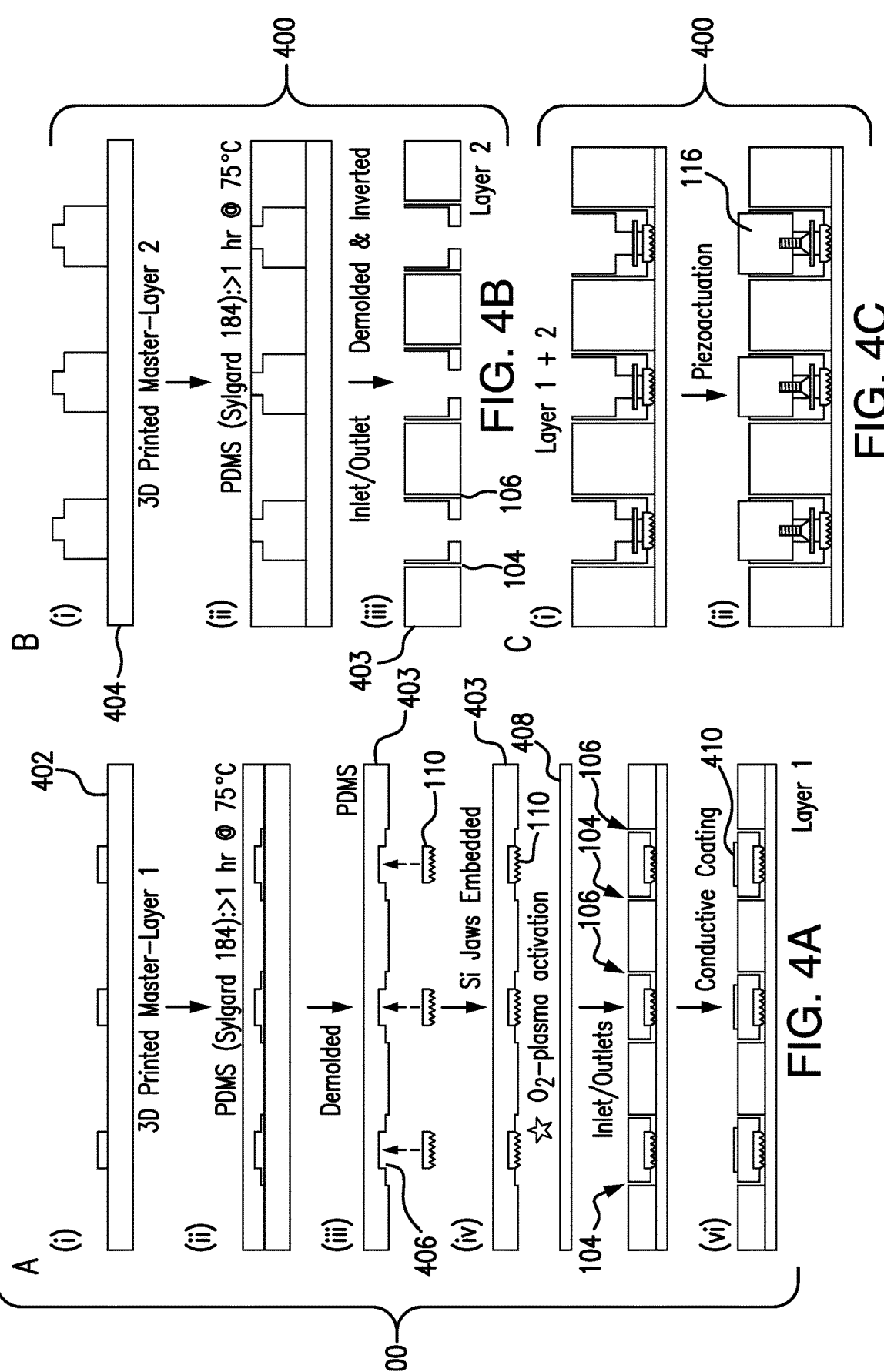
FIGS. 4A, 4B and 4C are schematics showing various steps involved in the fabrication and integration of different components in a system in accordance with the disclosure.
Figure 5:
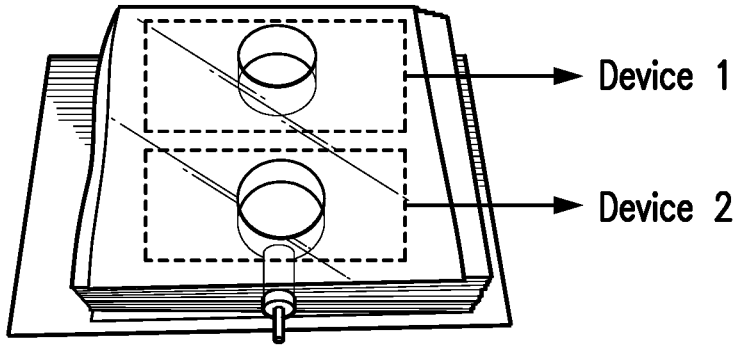
FIGS. 5 and 6 are outline views from different perspectives of a device in accordance with the disclosure.
Figure 6:
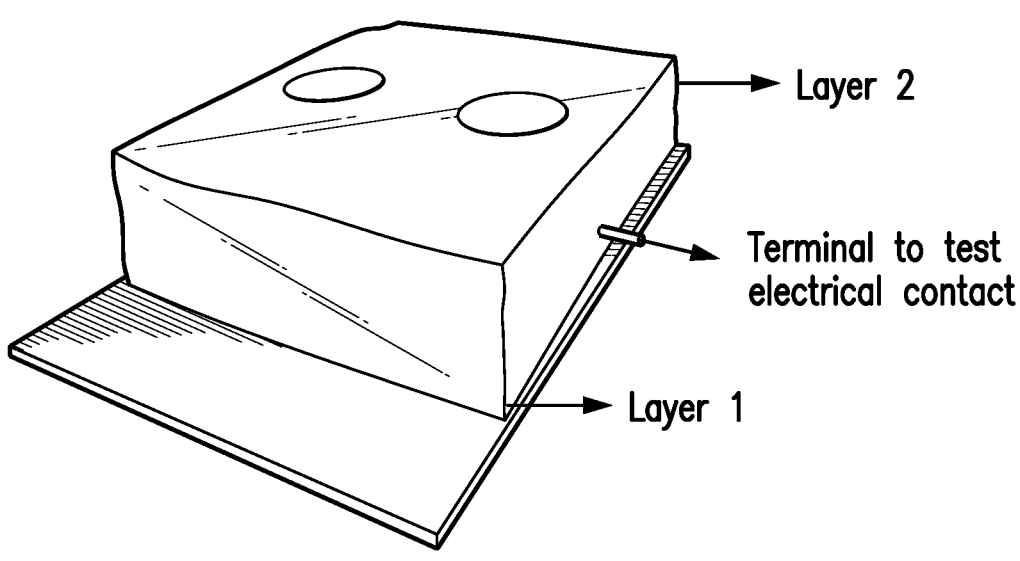

FIGS. 4A, 4B and 4C illustrate schematics of an exemplary process flow 400 to embed MEMS hardware into a soft microfluidic structure. A typical device consists of both soft elastomeric components (e.g., polydimethylsiloxane (PDMS), etc.), and hard brittle components (e.g., glass, patterned/etched Si die, metallic electrical contacts, etc.) as shown in FIG. 5 from a top view and in FIG. 6 from a side view.

In one embodiment, soft-lithography is used to fabricate the various elastomeric layers 403 from a 3D printed resin-based mold 402 or 404 (FIG. 4A(i) and FIG. 4B(i)). These elastomeric layers 403 can either have microchannel networks 406 or other features to enable easy integration of different components. The Si jaws, or hammer substrates 110, are embedded into one of the elastomeric layers 403, as shown in FIG. 4A(iii) and (iv), which is then bonded to a glass substrate 408 after punching inlets/outlets 104/106 using a biopsy punch (FIG. 4A(v)). A conductive layer 410 is painted on the elastomer surface above the Si Jaw (FIG. 4A(vi)). This layer is used to verify contact between the piezo head and the Si Jaw. The two elastomeric layers that have the Si Jaws, inlets/outlets, glass substrate, and the conductive coating are combined to form the final device or apparatus (100) 100, as shown in FIG. 4C.

During operation, the inlet channel(s) 104 and outlet channel(s) 106 are used to flow solutions that may have the test specimens (e.g., microbes) using mechanical flow pumps. The hammer substrate 110 or "jaws" in the apparatus 100 are used to mechanically lyse the cells included in the flow solutions. As previously described, when the piezo head or, in general, actuators 116 are activated, the Si jaws or hammer substrates 110 move and the microbes are squished between the Si jaws and the glass substrate, which serves as the anvil surface 112. Ideally this actuation will lead to the jaws perforating the microbial cell wall and thereby lysing the cell. Each chip can have multiple devices, for example, two devices, as shown in FIG. 5. The example shown here has two devices in one chip.

The following are certain aspects of the invention. In a first aspect, the disclosure describes an apparatus that comprises a frame, the frame forming an inlet channel, an outlet channel, and a processing chamber fluidly connected between the inlet and outlet channels, wherein the processing chamber includes an anvil surface formed on the frame. The apparatus (100) further comprises a hammer reciprocally mounted on the frame, the hammer having a processing surface disposed in opposed relation to the anvil surface; and an actuator connected to the frame and operably associated with the hammer, the actuator operating to move the hammer between a retracted position in which the processing surface is at a distance from the anvil surface, and an extended position in which the processing surface abuts the anvil surface (112).

A scanning electron (SE) microscope view of a hammer substrate 500 is shown in FIG. 7. In reference to this illustration, the substrate 500 was manufactured using a chrome mask having square cutouts, the square cutouts having sides of 1 μm and being spaced apart regularly on a square grid at 1 μm apart. Following etching, as can be seen in FIG. 7, a regular arrangement of a plurality of pillars 502 remain having flat heads 504 that are planarly aligned. As can be seen, the pillars 502 are arranged in spaced rows and columns in two dimensions following the original regular grid applied before the etching. Spaces 506 between the pillars 502 permit the passage of material through the pillars 502 during processing.

A SE microscope view of a hammer substrate 600 during a manufacturing step is shown in FIG. 8. In reference to this illustration, it can be seen that a series of parallel channels 602 are carved in parallel to one another and extending to a uniform depth 604 into a silicon wafer. After completion of the channel carving, a series of parallel walls 605 having a height of about the depth 604 from a working surface 606 remain. In a subsequent operation, the walls are broken to remove material. The brittle nature of the material leaves jagged and sharp edges and peaks extending away from the working surface 606 at the root of the walls 605 and provide the cutting and tearing elements that perform the lysis during operation. In the embodiment shown, the walls have a width of about 10 μm, are spaced apart at about 1 μm and extend at a depth of about 8.5 μm, but other dimensions can also be used. As can be appreciated, the subsequent operation can be omitted to leave generally smooth faces to provide the surface for lysis, in an embodiment.

Figures 9A, 9B:
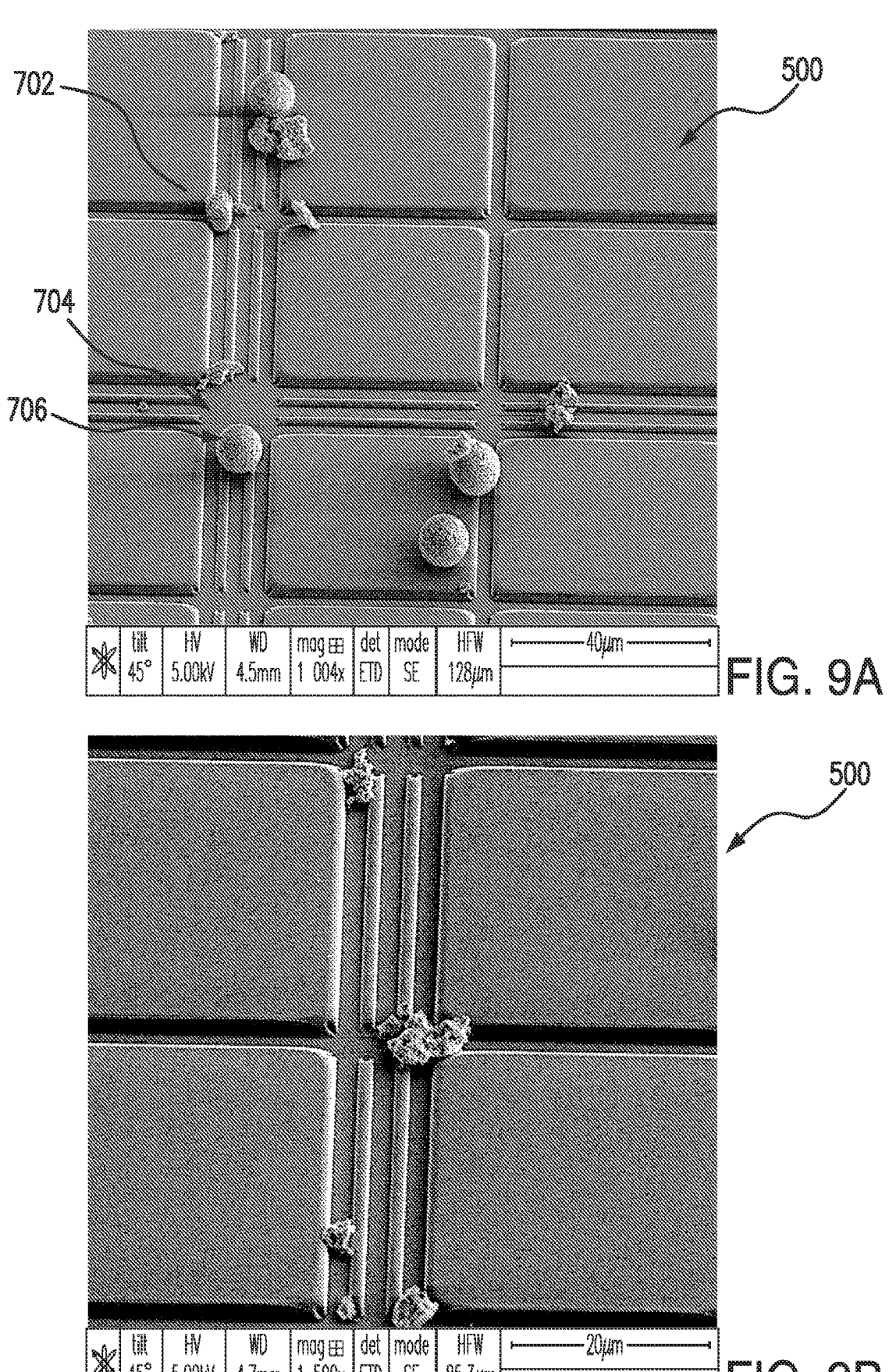
FIGS. 9A and 9B are visual illustrations of a crushing operation in accordance with the disclosure.
Figures 10A, 10B:
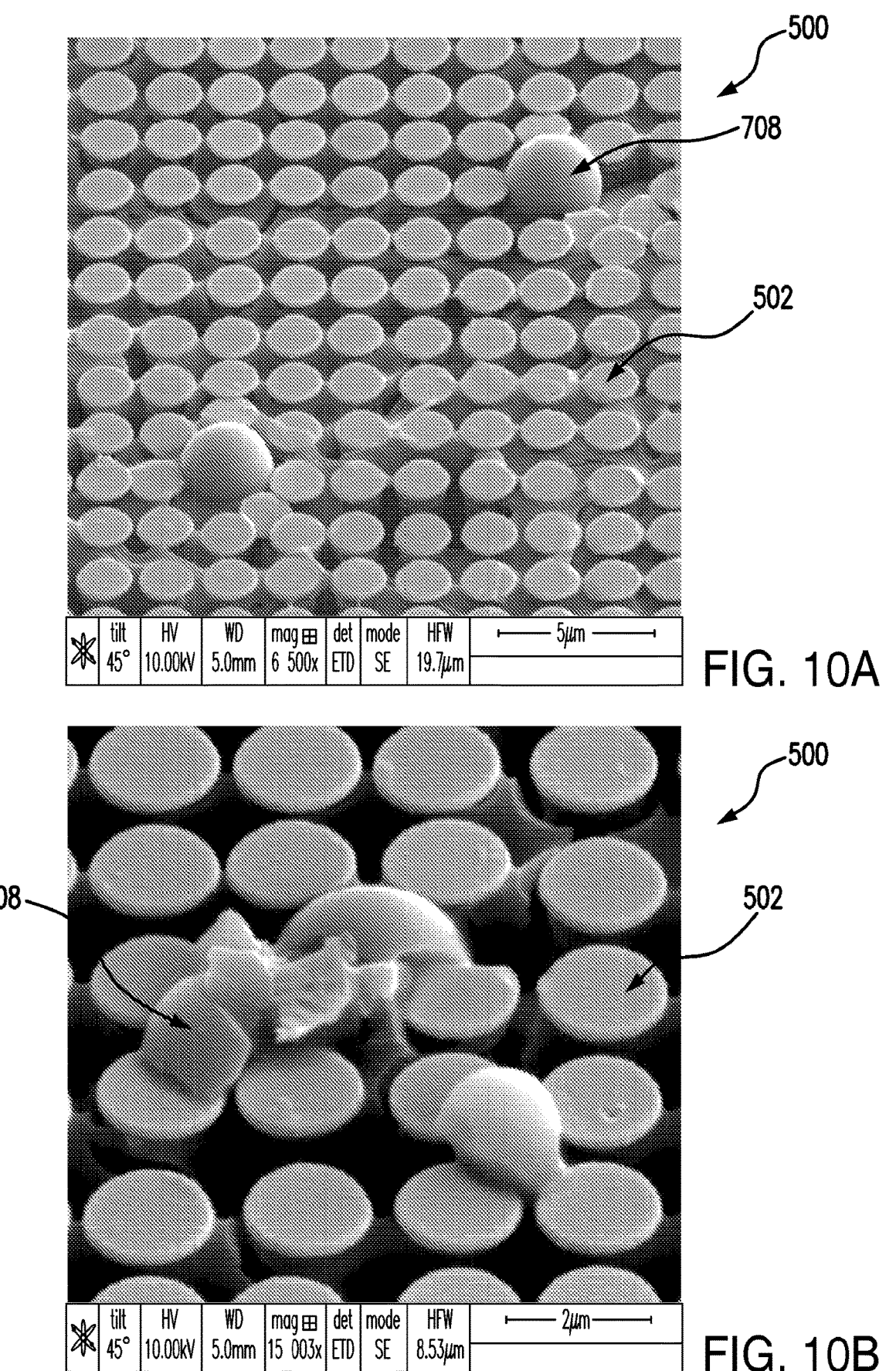
FIGS. 10A and 10B are visual illustrations of an additional crushing operation in accordance with the disclosure.

The exemplary embodiment according to the present disclosure were used to confirm that microbes or, in general, particles such as beads having a diameter of between 3-10 μm were successfully fractured using embodiments in accordance with the present disclosure. SE microscope scans are shown in FIGS. 9 and 10. More specifically, FIGS. 9A and 9B illustrate the hammer substrate 500 substrate in which the pillars 502 are arranged in groups or pads 702 and are separated by ridges 704 that are formed in grid pattern that includes single or multiple ridges 704 between the pads 702. As illustrated in FIG. 9A, beads 706 made from polymethyl methacrylate (PMMA) having an average diameter of about 10 μm, which simulate microbes, are placed on the hammer substrate 500 and are crushed as described herein between the substrate 500 and an anvil (not shown here). In FIG. 9B, it can be seen that the beads 706 are successfully crushed. An exemplary illustration in a crushing operation of porous SiO$_2$ beads 708 having an average diameter of about 3 μm on the hammer substrate 500 is shown in FIG. 10. Specifically, FIG. 10A shows the beads 708 placed on the pillars 502, and FIG. 10B shows the beads 708 after the pounding operation that is successful in shattering the beads 708. As can be seen in these illustrations, the beads 706 and 708, some of which were sized in range also of about 4-6 μm, and which simulate microbes in the range of anywhere within the range of 1-10 μm, are shattered by the pillars 502.

In a first aspect, the present disclosure describes an apparatus comprising a frame (102), the frame (102) forming an inlet channel (104), an outlet channel (106), and a processing chamber (108) fluidly connected between the inlet and outlet channels (104). The processing chamber (108) includes an anvil surface (112) formed on the frame (102). A hammer (110) is mounted on the frame (102), the hammer (110) having a processing surface disposed in opposed relation to the anvil surface (112), the hammer (110) configured to move relative to the anvil surface (112). The apparatus further comprises an actuator (116) connected to the frame (102) and operably associated with the hammer (110), the actuator operating to move the hammer (110) relative to the anvil surface (112) and in close proximity to the anvil surface (112). In one embodiment, the hammer (110) operates between a retracted position in which the processing surface is at a distance from the anvil surface (112), and an extended position in which the processing surface abuts the anvil surface (112).

In one embodiment, the processing surface includes at least one of a plurality of pointed structures adapted to perforate microbes present between the hammer (110) and the anvil surface (112), and/or a plurality of blunted or flat structures adapted to crush microbes present between the hammer (110) and the anvil surface.

In the apparatus in accordance with the first aspect, the anvil surface may be made of glass, the actuator may be configured for motion that is at least one of linear along a direction, and rotational, and/or a mechanical action of the hammer against the anvil may be configured to mechanically interact with microbes that flow within the microfluidic channel, such mechanical interaction including piercing, crushing, shear interaction, and rotational interaction.

In the apparatus in accordance with the first aspect, the hammer may be made from a rigid material selected from the group consisting of metal, silicon, ceramic oxide substrate, and a semiconductor, the frame may be made from an elastomeric material, and the hammer may be made from a silicon <100> oriented wafer. In one embodiment, the hammer may include a plurality of structures having jagged, sharp non-systematic tips, in close relation to the anvil surface.

In a second aspect, the present disclosure describes a method for use of the apparatus (100) in accordance with the first aspect to mechanically perform cell lysis. The method includes providing the frame (102) forming an inlet channel (104), an outlet channel (106), and a processing chamber (108) fluidly connected between the inlet and outlet channels (104), wherein the processing chamber (108) includes an anvil surface formed on the frame (102). The method further includes providing the hammer mounted on the frame (102), the hammer having a processing surface disposed in opposed relation to the anvil surface, and providing an actuator connected to the frame and operably associated with the hammer, the actuator operating to move the hammer in close relation relative to the anvil surface for tearing, piercing, and/or crushing microbes adapted to be provided between the hammer and the anvil surface.

In an embodiment according to the second aspect, the method further includes performing cell lysis by providing microbes through the inlet channel (104) and directing the microbes through the processing chamber (108), processing the microbes by activating the actuator, and collecting crushed or perforated microbe material at the outlet channel (106).

In accordance with the method of the second aspect of the disclosure, activating the actuator may include activating the actuator to at least one of move the hammer along one or more directions, and rotating the hammer along a vertical direction and/or a horizontal direction. The crushed microbes can have an average size of between 1-10 μm.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus, comprising:
   a frame, the frame forming an inlet channel, an outlet channel, and a processing chamber fluidly connected between the inlet and outlet channels, wherein the processing chamber includes an anvil surface formed on the frame;
   a hammer mounted on the frame, the hammer having a processing surface disposed in opposed relation to the anvil surface, the hammer configured to move relative to the anvil surface; and
   an actuator connected to the frame and operably associated with the hammer, the actuator operating to move the hammer relative to the anvil surface and in close proximity to the anvil surface, wherein the hammer operates between a retracted position in which the processing surface is at a distance from the anvil surface, and an extended position in which the processing surface abuts the anvil surface.

2. The apparatus of claim 1, wherein the processing surface includes at least one of a plurality of pointed structures adapted to perforate microbes present between the hammer and the anvil surface, and/or a plurality of blunted or flat structures adapted to crush microbes present between the hammer and the anvil surface.

3. The apparatus of claim 1, wherein the anvil surface is made of glass.

4. The apparatus of claim 1, wherein the actuator is configured for motion that is at least one of linear along a direction, and rotational.

5. The apparatus of claim 1, wherein a mechanical action of the hammer against the anvil is configured to mechanically interact with microbes that flow within the microfluidic channel, such mechanical interaction including piercing, crushing, shear interaction, and rotational interaction.

6. The apparatus of claim 1, wherein the hammer is made from a rigid material is selected from the group consisting of metal, silicon, ceramic oxide substrate, and a semiconductor.

7. The apparatus of claim 1, wherein the frame is made from an elastomeric material.

8. The apparatus of claim 1, wherein the hammer is made from a silicon oriented wafer.

9. The apparatus of claim 1, wherein the hammer includes a plurality of structures having jagged, sharp non-systematic tips, in close relation to the anvil surface.

10. A method for use of an apparatus of claim 1 to mechanically perform cell lysis, the method comprising:
   providing the frame forming an inlet channel, an outlet channel, and a processing chamber fluidly connected between the inlet and outlet channels, wherein the processing chamber includes an anvil surface formed on the frame;
   providing the hammer mounted on the frame, the hammer having a processing surface disposed in opposed relation to the anvil surface; and
   providing an actuator connected to the frame and operably associated with the hammer, the actuator operating to move the hammer in close relation relative to the anvil surface for tearing, piercing, and/or crushing microbes adapted to be provided between the hammer and the anvil surface;
   performing cell lysis by providing microbes through the inlet channel and directing the microbes through the processing chamber;
   processing the microbes by activating the actuator; and
   collecting crushed or perforated microbe material at the outlet channel.

11. The method of claim 10, wherein activating the actuator includes activating the actuator to at least one of move the hammer along one or more directions, and rotating the hammer along a vertical direction and/or a horizontal direction.

12. The method of claim 10, wherein the microbes have an average size between 1-10 $\mu$m.

* * * * *